(12) United States Patent
Zowtiak et al.

(10) Patent No.: US 6,334,441 B1
(45) Date of Patent: *Jan. 1, 2002

(54) PHONATION VALVE FOR BREATHING TUBE

(75) Inventors: John Zowtiak, Coto De Caza; Thomas Young, Corona; Tony Wondka, Mountain View, all of CA (US)

(73) Assignee: Mallinckrodt Medical, Inc., St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/197,669

(22) Filed: Nov. 23, 1998

(51) Int. Cl.$^7$ ............................................... A61M 16/00
(52) U.S. Cl. .......................... 128/207.16; 128/207.12; 128/205.24; 623/9
(58) Field of Search ................. 128/207.14, 207.15, 128/207.16, 205.24, 207.12, 201.19, 205.11; 623/9; 137/854

(56) References Cited

U.S. PATENT DOCUMENTS

| | | | |
|---|---|---|---|
| 3,137,299 A | | 6/1964 | Tabor |
| 3,356,100 A | * | 12/1967 | Seeler |
| 3,924,637 A | | 12/1975 | Swanson |
| 3,952,335 A | | 4/1976 | Sorce et al. |
| 3,990,439 A | | 11/1976 | Klinger |
| 4,040,428 A | | 8/1977 | Clifford |
| 4,190,045 A | | 2/1980 | Bartels |
| 4,259,951 A | | 4/1981 | Chernack et al. |
| 4,325,366 A | | 4/1982 | Tabor |
| 4,538,607 A | | 9/1985 | Saul |
| 4,627,433 A | | 12/1986 | Lieberman |
| 4,759,356 A | | 7/1988 | Muir |
| 4,838,262 A | * | 6/1989 | Katz ...................... 128/205.24 |
| 4,971,054 A | | 11/1990 | Andersson et al. |
| 5,059,208 A | * | 10/1991 | Coe et al. ....................... 623/9 |
| 5,107,828 A | * | 4/1992 | Koss et al. ............ 128/200.26 |
| 5,231,982 A | * | 8/1993 | Harrison ................ 128/207.12 |
| 5,259,378 A | | 11/1993 | Huchon et al. |
| 5,385,141 A | * | 1/1995 | Granatiero ............. 128/201.19 |
| 5,392,775 A | * | 2/1995 | Adkins, Jr. et al. ..... 128/207.16 |
| 5,771,888 A | * | 6/1998 | Keim .................... 128/207.15 |
| 5,957,978 A | * | 9/1999 | Blom ............................. 623/9 |

FOREIGN PATENT DOCUMENTS

GB      1146683      3/1969

* cited by examiner

*Primary Examiner*—John G. Weiss
*Assistant Examiner*—V. Srivastava
(74) *Attorney, Agent, or Firm*—Rothwell, Figg, Ernst & Manbeck

(57) ABSTRACT

In accordance with the present invention, a phonation valve which is cooperatively connectable to a breathing tube connected to a patient's airway, includes a valve body having first and second ends through which gas passes into and out of the valve. The first end is connectable to the breathing tube for passage of gas between the breathing tube and the valve. A valve seat is located within the valve body between the first and second ends. A thin, flexible diaphragm is provided, which is seated against the valve seat when the patient exhales. The diaphragm has a comfort-improving structural feature which can be 1) a shape which is at least partly concave on a side of the diaphragm facing the seat, and/or 2) a web of substantially uniform thickness with a plurality of discrete areas of different thicknesses dispersed around the web, which are capable of damping resonance vibration of the diaphragm during breathing by the patient.

11 Claims, 6 Drawing Sheets

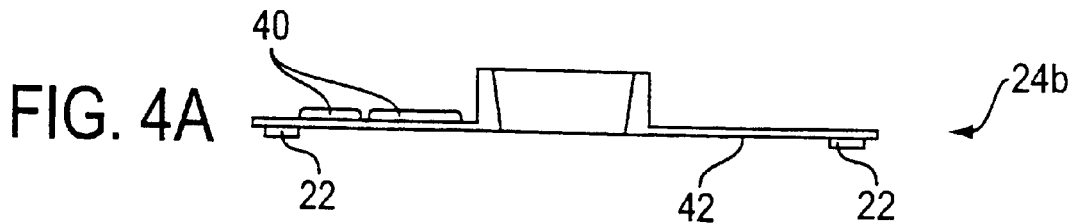
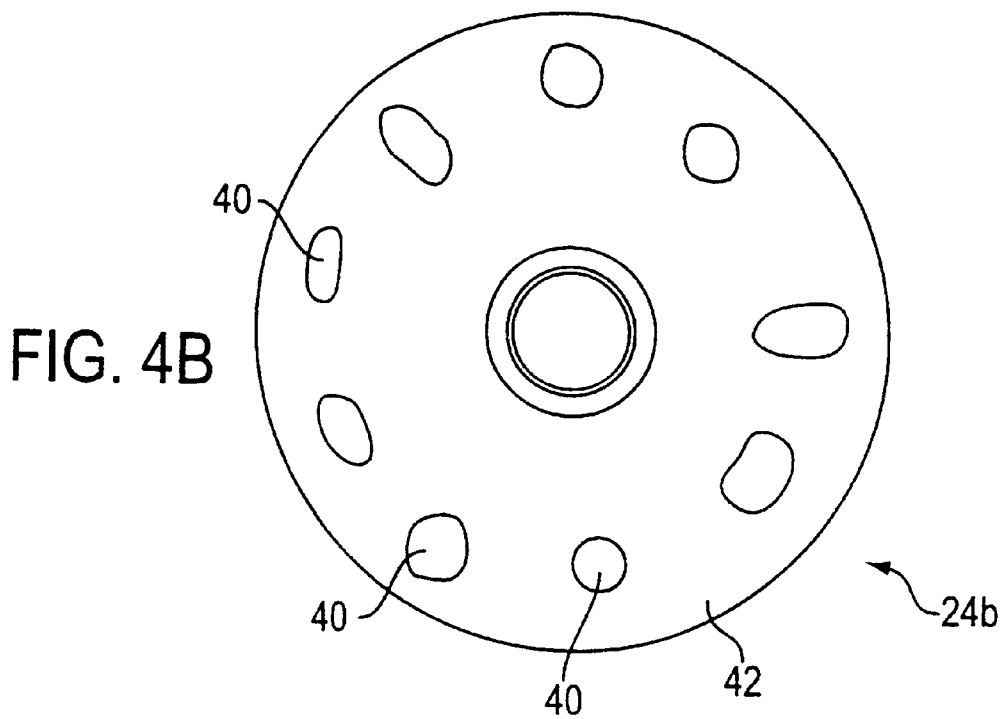

PHONATION VALVE FOR BREATHING TUBE

BACKGROUND OF THE INVENTION

1. Field of the Invention

The present invention relates to a phonation valve for a breathing tube such as a tracheostomy tube.

2. Description of the Background Art

Phonation valves permit speaking by a patient having a breathing tube inserted into the patient's airway, such as a tracheostomy tube inserted into a patient's trachea.

Various valves for tracheostomy tubes are known in the art, including those disclosed in U.S. Pat. Nos. 3,137,299, 4,040,428, 4,325,366, 4,759,356, 4,971,054 and 5,259,378.

Phonation valves such as disclosed in U.S. Pat. No. 3,137,299 include a flapper-type valve diaphragm, which permits the patient to inhale through the valve, but closes on exhalation, thereby forcing air past the vocal cords and permitting the patient to speak.

Phonation valves with flat flapper-type valve diaphragms sometimes allow harmonic vibration noise during exhalation because of the natural vibration frequency of the diaphragm.

Harmonic vibration noise during exhalation resulting from natural vibration frequencies of the diaphragm can be reduced or eliminated by biasing the diaphragm against the valve seat. U.S. Pat. No. 4,759,356 discloses a phonation valve having a diaphragm which is biased toward the valve seat so that the valve diaphragm has a convex shape on the side of the diaphragm facing the valve seat. However, valves having diaphragms which are produced flat, and pre-loaded (biased) against the valve seat to prevent harmonic vibration during exhalation, can result in high cracking pressure to open the valve, with resulting uncomfortable breathing resistance for the patient.

There remains a need in the art for improvements in phonation valves.

SUMMARY OF THE INVENTION

In accordance with the present invention, a phonation valve which is cooperatively connectable to a breathing tube connected to a patient's airway, comprises a valve body having first and second ends through which gas passes into and out of the valve. The first end is connectable to the breathing tube for passage of gas between the breathing tube and the valve. A valve seat is located within the valve body between the first and second ends. A thin, flexible diaphragm is provided, which is seated against the valve seat when the patient exhales. The diaphragm has comfort-improving structural features which may include: 1) a shape which is at least partly concave on a side of the diaphragm facing the seat, and/or 2) a web of substantially uniform thickness with a plurality of discrete areas of different thicknesses dispersed around the web, which are capable of damping resonance vibration of the diaphragm during breathing by the patient.

BRIEF DESCRIPTION OF THE DRAWINGS

FIG. 4A is a side elevational view, partly schematic, of a flexible diaphragm in accordance with one embodiment.

FIG. 4B is a bottom elevational view of the flexible diaphragm shown in FIG. 4A.

DETAILED DESCRIPTION OF THE PREFERRED EMBODIMENTS

Figure 1:
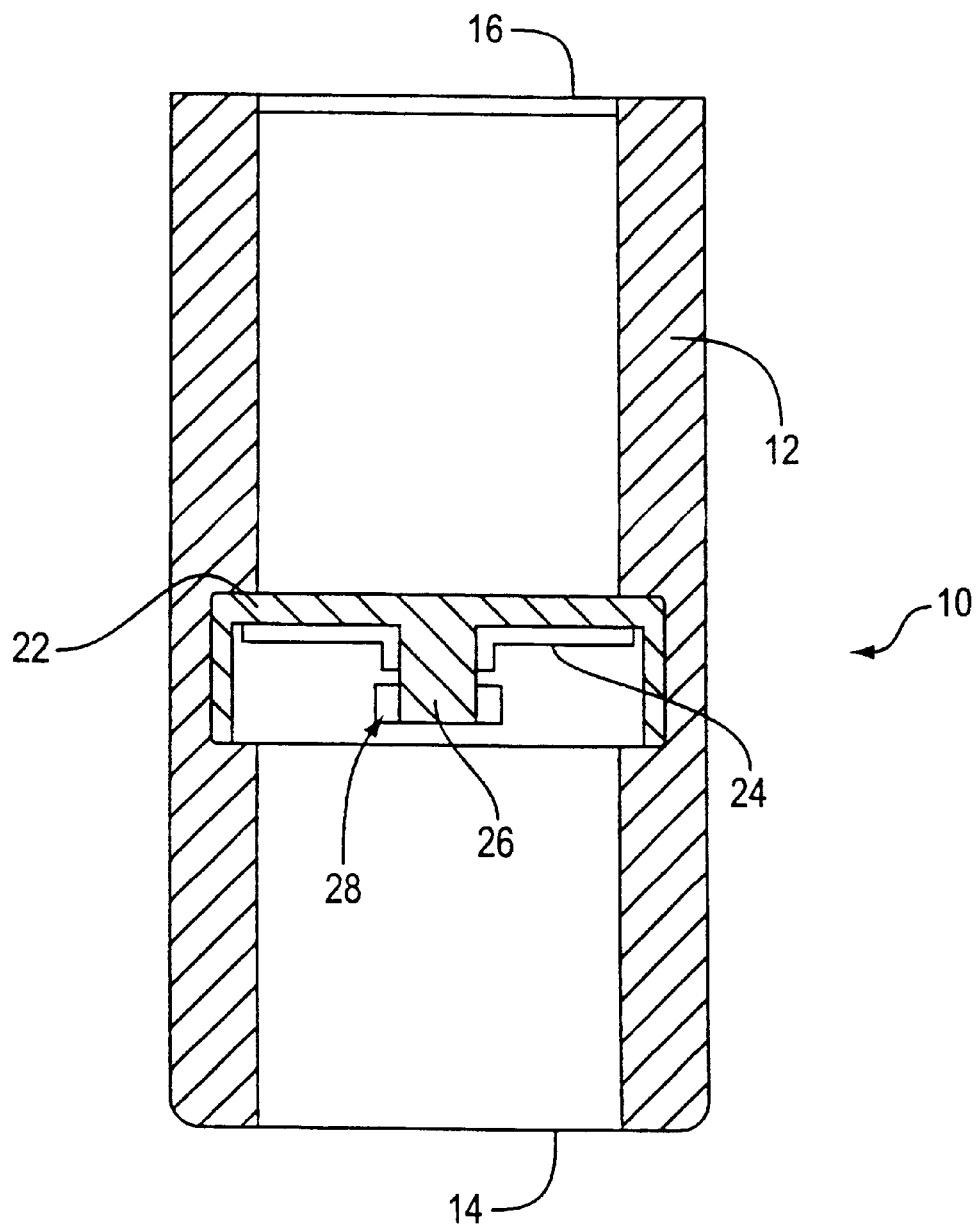
FIG. 1 is a cross-sectional view, partly schematic, of a phonation valve in accordance with one embodiment of the present invention.

FIG. 1 shows a phonation valve 10 in accordance with one embodiment of the present invention. Phonation valve 10 includes a valve body 12 having first and second ends 14 and 16 respectively, through which gas, such as air, or oxygen, passes into and out of valve 10.

Figure 2:
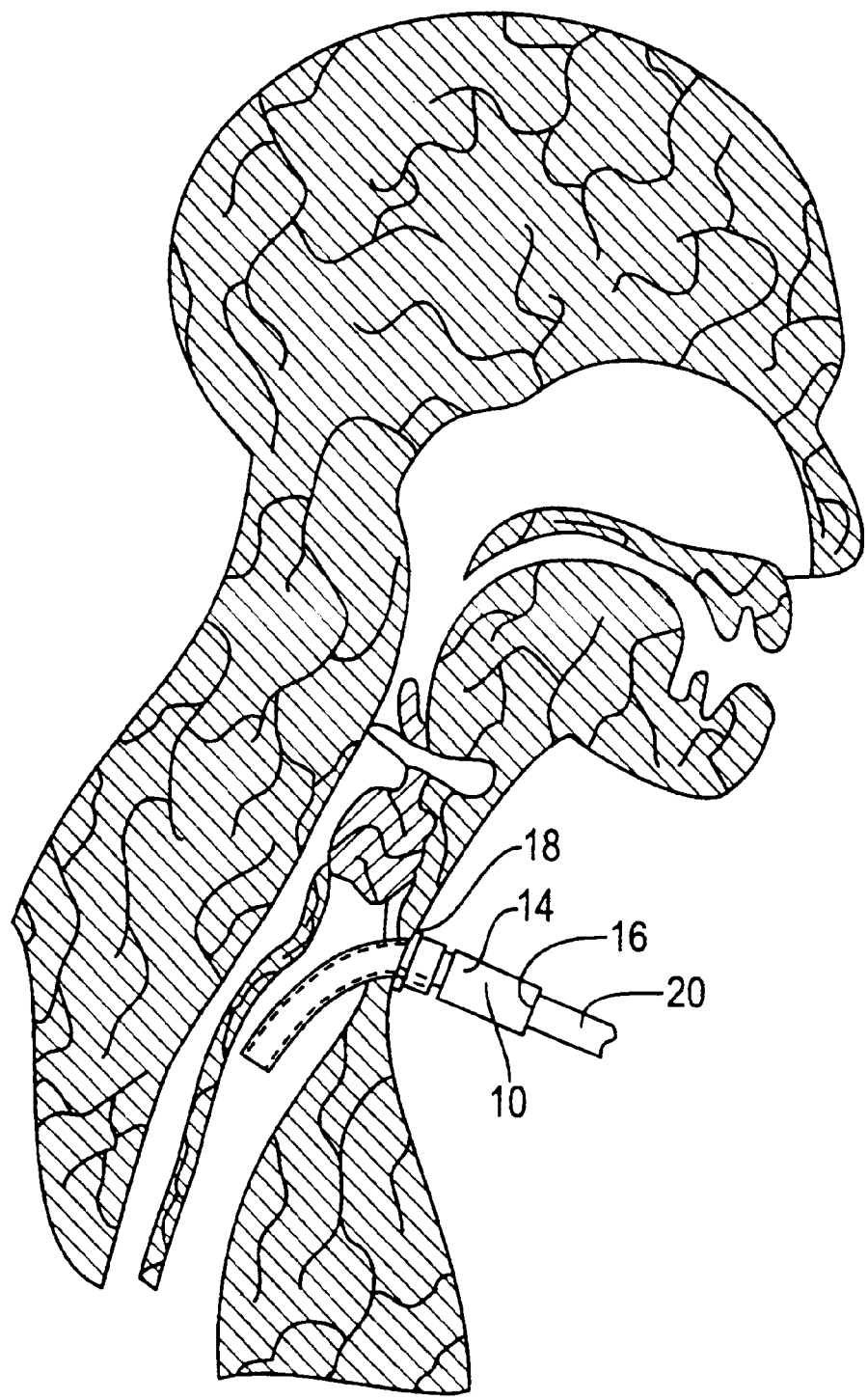
FIG. 2 is a schematic illustration, partially in cross-section, showing use of a valve in accordance with the present invention.

The first end 14 of valve 10 is connectable to a breathing tube such as tracheostomy tube 18 shown in FIG. 2.

In the embodiment shown, phonation valve 10 is an in-line phonation valve wherein the second end 16 is connectable to a source of gas such as oxygen (not shown) by line 20. However, the invention is equally applicable to end-fitting phonation valves which, for example, can be attached to the end of a breathing tube such as tracheostomy tube 18, and which are not connectable to another line such as line 20.

Referring back to FIG. 1, a valve seat 22 is located within the valve body 12 between the first and second ends 14 and 16 respectively. A thin, flexible diaphragm 24 is mounted circumferentially around a stem 26, and can be held onto stem 26 by protrusion 28 or any other suitable means.

The diaphragm 24 can be formed of any suitable thin, flexible material, such as silicone rubber, and can have any suitable thickness, such as about 0.005–0.02 inch.

The present invention provides a patient with comfort-improving structural features which require reduced cracking pressures to open the valve when inhaling, and reduce or prevent harmonic vibration noise from occurring during use.

Figure 3A:
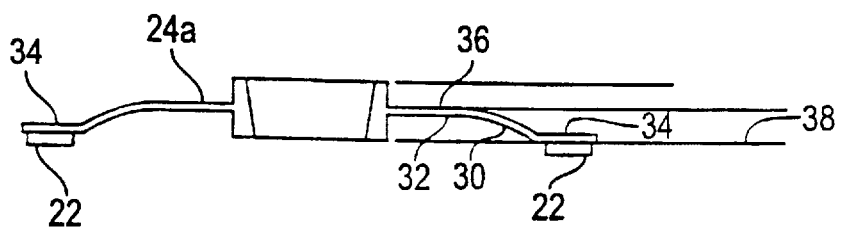
FIG. 3A is a side elevational view, partly schematic, of a flexible diaphragm in accordance with one embodiment.
Figure 3B:
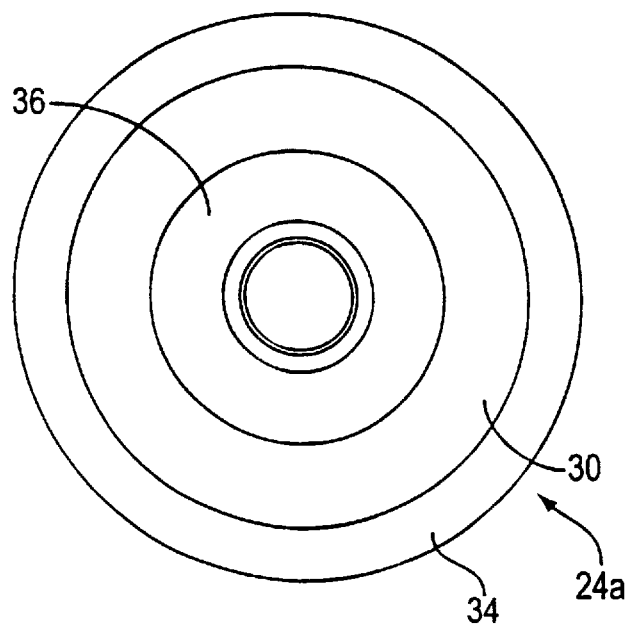
FIG. 3B is a bottom elevational view of the flexible diaphragm shown in FIG. 3A.

FIGS. 3A and 3B show a diaphragm 24a which is partly concave about its circumference in region 30 on a side 32 of diaphragm 24a facing valve seat 22.

A diaphragm as shown in FIGS. 3A and 3B is seated against valve seat 22 when the diaphragm is at rest. According to this embodiment, an outer annular edge region 34 of the diaphragm, comprising a relatively small amount of the diaphragm mass, is positioned against the valve seat 22 in the closed position whereas the remaining bulk of the diaphragm mass comprised of concave portion 30 and the annular inner diaphragm portion 36 is positioned away from the plane 38 of valve seat 22. Accordingly, most of the diaphragm mass is positioned away from the plane 38 of valve seat 22 as the annular diaphragm edge region 34 is positioned against valve seat 22 while the valve is at rest, thus giving the valve a "closed" condition. During inspiration, a relatively small amount of diaphragm mass is required to move to the open position, thereby reducing the cracking pressure to open, reducing the pressure drop once the valve is in the open position. Furthermore, by having the diaphragm seated against the valve seat when the diaphragm is at rest, a "natural" seal is maintained while the valve is at rest, reducing or eliminating leakage and associated vibration noise.

FIGS. 4A and 4B show another embodiment wherein a plurality of discrete areas 40 of different thicknesses are provided on a flat (planar) diaphragm 24b. In the embodiment shown in FIGS. 4A and 4B, diaphragm 24b has a web portion 42 which is of substantially uniform thickness, e.g., 0.008 inch. The discrete areas 40 are in the form of raised bumps which are distributed on the web 42, and are randomly spaced and sized to dynamically dampen the diaphragm mass such that during exhalation, a harmonic frequency and resultant vibration resonance of the diaphragm does not occur. As can be seen in FIG. 4A, the bumps have a thickness dimension which is substantially greater than the thickness dimension of the web portion 42. Additionally, it can be seen that the bumps are non-uniformly distributed over the surface of web 42. Bumps 40, in preferred embodiments, are of different sizes and are randomly spaced with respect to each other, so as to avoid vibrational resonance of the diaphragm.

Figure 5A:
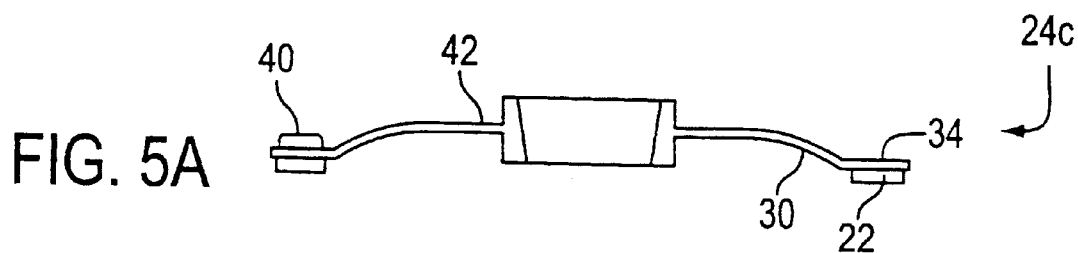
FIG. 5A is a side elevational view, partly schematic, of a flexible diaphragm in accordance with one embodiment.
Figure 5B:
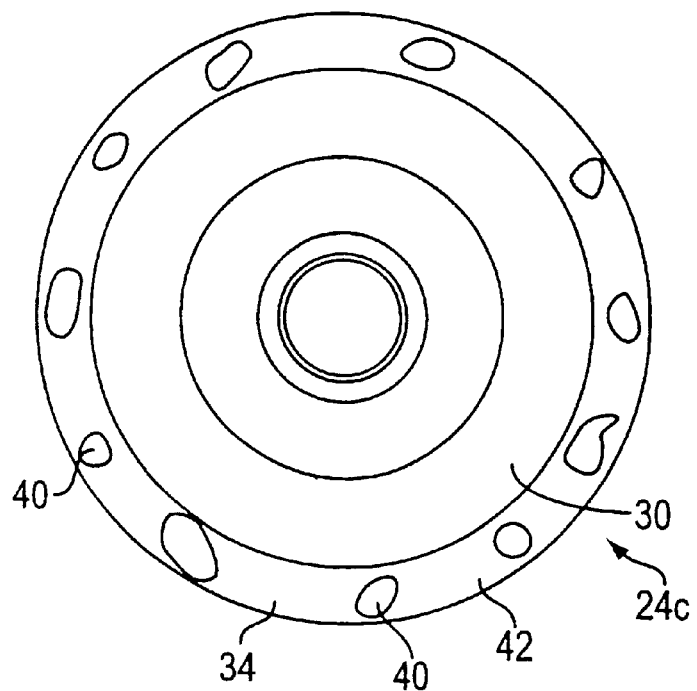
FIG. 5B is a bottom elevational view of the flexible diaphragm shown in FIG. 5A.

FIGS. 5A and 5B shown a combination diaphragm 24c having bumps 40 as described above with respect to FIGS. 4A and 4B. The bumps 40 shown in FIGS. 5A and 5B are located about the annular edge portion 34 of diaphragm 24c. According to this embodiment, diaphragm 24c also has a concave portion 30 as described above with reference to FIGS. 3A and 3B.

Figure 6A:
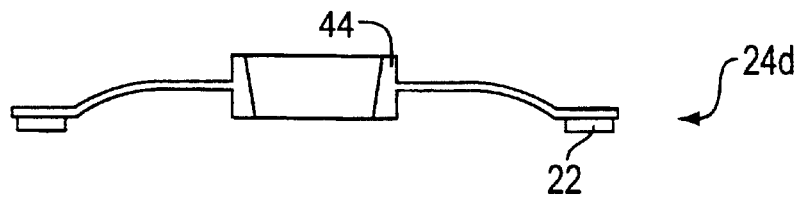
FIG. 6A is a side elevational view, partly schematic, of a flexible diaphragm in accordance with one embodiment.
Figure 6B:
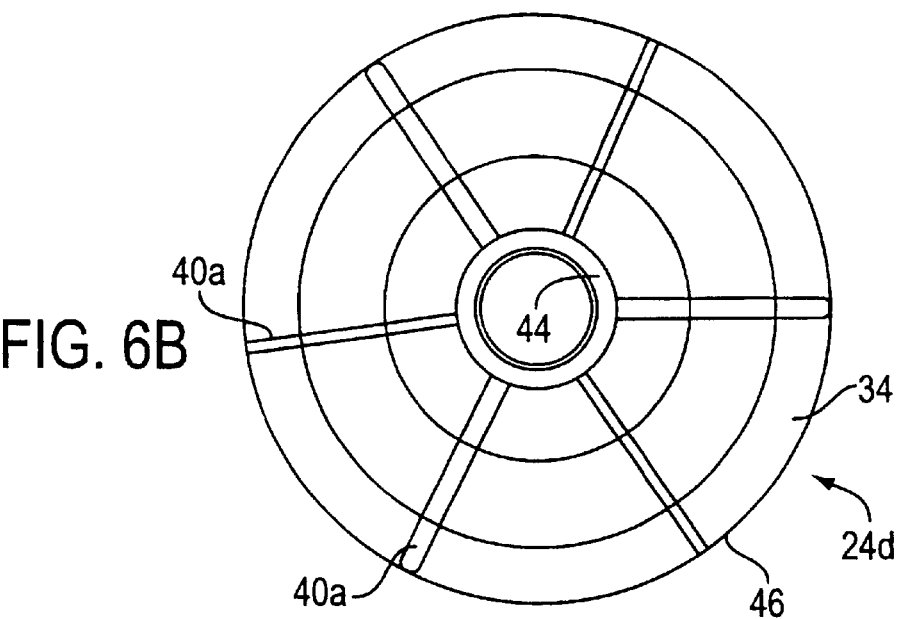
FIG. 6B is a bottom elevational view of the flexible diaphragm shown in FIG. 6A.
Figure 6C:
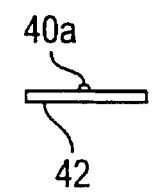
FIG. 6C is a side elevational schematic view of a portion of the diaphragm shown in FIG. 6B.
Figure 6D:
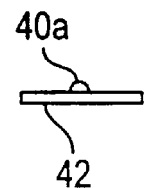
FIG. 6D is a side elevational schematic view of a portion of the diaphragm shown in FIG. 6B.

In the embodiments shown in FIGS. 6A, 6B, 6C, and 6D, the bumps are comprised of radially extending ribs 40a, which extend from the central collar 44 of the diaphragm to the outer edge 46 of annular edge portion 34. As can be seen in FIGS. 6B, 6C and 6D, rib bumps 40a can be of different thicknesses and widths with respect to each other, and are non-uniformly spaced circumferentially with respect to diaphragm 24d, so as to reduce or eliminate harmonic vibration and resultant noise during use.

The present invention provides a phonation valve which improves a patient's comfort during use by providing reduced cracking pressures to open the valve, as well as a reduction or elimination of harmonic vibration of the diaphragm and resultant noise during use.

What is claimed is:

1. A phonation valve cooperatively connectable to a breathing tube connected to a patient's airway, the valve comprising
   a valve body having first and second ends through which ends gas passes into and out of said valve body, the first end connectable to said breathing tube for passage of gas between said breathing tube and said valve body;
   a valve seat having a circumference, and being located within said valve body between said first and second ends;
   a thin, flexible diaphragm having a circumference, and having a planar edge region which extends completely around the circumference of the diaphragm and is located on a substantially planar diaphragm portion which extends completely around the circumference of the diaphragm, the diaphragm including a mounting structure located centrally in said diaphragm, for mounting the diaphragm in said valve body with said planar edge region of said diaphragm being circumferentially positioned about said mounting structure, the planar edge region of the diaphragm being seated against said valve seat when the patient exhales, said diaphragm having a comfort-improving structural feature which is selected from the group consisting of 1) a concave portion extending completely circumferentially around said mounting structure from said mounting structure to said planar edge region of said diaphragm such that most of the diaphragm mass is positioned away from the plane of said valve seat, said concave portion being located on a side of said diaphragm facing said valve seat, 2) a web of substantially uniform thickness with a plurality of discrete areas of different thicknesses dispersed around the web, which are capable of damping resonance vibration of said diaphragm during breathing by said patient, and which are located at least on said substantially planar diaphragm portion which extends completely around the circumference of the diaphragm, and 3) a combination of 1) and 2).

2. The phonation valve of claim 1 wherein said diaphragm has said at least partly concave shape and is seated against said valve seat when said diaphragm is at rest.

3. A phonation valve cooperatively connectable to a breathing tube connected to a patient's airway, the valve comprising
   a valve body having first and second ends through which ends gas passes into and out of said valve body, the first end connectable to said breathing tube for passage of gas between said breathing tube and said valve body;
   a valve seat having a circumference, and being located within said valve body between said first and second ends;
   a thin, flexible diaphragm having a circumference, and having a planar edge region which extends completely around the circumference of the diaphragm and is located on a substantially planar diaphragm portion which extends completely around the circumference of the diaphragm, the diaphragm including a mounting structure located centrally in said diaphragm, for mounting the diaphragm in said valve body with said planar edge region of said diaphragm being circumferentially positioned about said mounting structure, the planar edge region of the diaphragm being seated against said valve seat when the patient exhales, said diaphragm having a comfort-improving structural feature which is selected from the group consisting of 1) an at least partly concave portion of said diaphragm extending completely circumferentially around said mounting structure between said mounting structure and said planar edge region of said diaphragm, said at least partly concave portion being located on a side of said diaphragm facing said valve seat, 2) a web of substantially uniform thickness with a plurality of discrete areas of different thicknesses dispersed around the web, which are capable of damping resonance vibration of said diaphragm during breathing by said patient, and which are located at least on said substantially planar diaphragm portion which extends completely around the circumference of the diaphragm, and 3) a combination of 1) and 2);
   wherein said diaphragm has a web portion of substantially uniform thickness, and a plurality of bumps distributed on one side of said web, said diaphragm having thickness dimensions at said bumps which are substantially greater than a thickness dimension of said web portion.

4. The phonation valve of claim 3 wherein at least a portion of said bumps are non-uniformly distributed about said web portion.

5. The phonation valve of claim 4 wherein said bumps are comprised of radially extending ribs.

6. The phonation valve of claim 3 wherein at least a portion of said bumps are of different size with respect to others of said bumps.

7. The phonation valve of claim 6 wherein at least a portion of said bumps are of different thicknesses with respect to others of said bumps.

8. The phonation valve of claim 7 wherein said bumps are comprised of radially extending ribs.

9. The phonation valve of claim 8 wherein said ribs are non-uniformly circumferentially spaced about said diaphragm.

10. The phonation valve of claim 3 wherein at least a portion of said bumps are of different thicknesses with respect to others of said bumps.

11. A phonation valve cooperatively connectable to a breathing tube connected to a patient's airway, the valve comprising a valve body having first and second ends through which ends gas passes into and out of said valve body, the first end connectable to said breathing tube for passage of gas between said breathing tube and said valve body;

a valve seat having a circumference, and being located within said valve body between said first and second ends;

a thin, flexible diaphragm having a circumference, and having a planar edge region which extends completely around the circumference of the diaphragm and is located on a substantially planar diaphragm portion which extends completely around the circumference of the diaphragm, the diaphragm including a mounting structure located centrally in said diaphragm, for mounting the diaphragm in said valve body with said planar edge region of said diaphragm being circumferentially positioned about said mounting structure, the planar edge region of the diaphragm being seated against said valve seat when the patient exhales, said diaphragm having a comfort-improving structural feature which is 1) an at least partly concave portion of said diaphragm extending completely circumferentially around said mounting structure between said mounting structure and said planar edge region of said diaphragm, said at least partly concave portion being located on a side of said diaphragm facing said valve seat, and 2) a web of substantially uniform thickness with a plurality of discrete areas of different thicknesses dispersed around the web, which are capable of damping resonance vibration of said diaphragm during breathing by said patient, and which are located at least on said substantially planar diaphragm portion which extends completely around the circumference of the diaphragm.

\* \* \* \* \*